(12) United States Patent
Song et al.

(10) Patent No.: US 11,737,184 B2
(45) Date of Patent: *Aug. 22, 2023

(54) LED LIGHTING APPARATUS AND LIGHTING SYSTEM HAVING THE SAME

(71) Applicant: Seoul Semiconductor Co., Ltd., Ansan-si (KR)

(72) Inventors: Jun Ho Song, Ansan-si (KR); Bo Yong Han, Ansan-si (KR)

(73) Assignee: Seoul Semiconductor Co., Ltd., Ansan-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 17/827,194

(22) Filed: May 27, 2022

(65) Prior Publication Data

US 2022/0295613 A1    Sep. 15, 2022

Related U.S. Application Data (63) Continuation of application No. 16/793,329, filed on Feb. 18, 2020, now Pat. No. 11,350,496.

(Continued)

(51) Int. Cl.
*H05B 45/20* (2020.01)
*H01L 33/50* (2010.01)
(Continued)

(52) U.S. Cl.
CPC ............ *H05B 45/20* (2020.01); *A61L 2/0047* (2013.01); *A61L 2/0052* (2013.01); *A61L 2/24* (2013.01);
(Continued)

(58) Field of Classification Search
CPC ....... H05B 45/20; H05B 47/11; A61L 2/0047; A61L 2/0052; A61L 2/24; A61L 2202/11;
(Continued)

(56) References Cited

U.S. PATENT DOCUMENTS

| 10,371,325 B1 | 8/2019 | Yuan et al. |
| 10,420,184 B1 | 9/2019 | Soler et al. |

(Continued)

FOREIGN PATENT DOCUMENTS

| JP | 6462713 | 1/2019 |
| KR | 10-2010-0051476 | 5/2010 |

(Continued)

OTHER PUBLICATIONS

Non-Final Office Action dated Jul. 17, 2020, in U.S. Appl. No. 16/793,329.

(Continued)

*Primary Examiner* — Donald L Raleigh
(74) *Attorney, Agent, or Firm* — H.C. Park & Associates, PLC (57) ABSTRACT

A lighting apparatus including a controller, an LED driver, and an LED luminaire including: a first light emitting unit for general lighting; and at least one of a second light emitting unit to cause production of vitamin D upon irradiation, a third light emitting unit to cause production of a cell activating substance upon irradiation, and a fourth light emitting unit to sterilize pathogenic microorganisms, in which the controller controls the LED driver to change a color temperature of the first light emitting unit in accordance with a change in a color temperature of sunlight, and to change an irradiance of light emitted from at least one of the second, third, and fourth light emitting units according to time, and the LED luminaire includes a greater number of the first light emitting unit than any of the second, third, and fourth light emitting units.

20 Claims, 6 Drawing Sheets

Related U.S. Application Data (60) Provisional application No. 62/807,333, filed on Feb. 19, 2019.

(51) Int. Cl.

| | | |
|---|---|---|
| *A61L 2/00* | (2006.01) | |
| *A61L 2/24* | (2006.01) | |
| *A61N 5/06* | (2006.01) | |
| *F21V 23/00* | (2015.01) | |
| *F21Y 115/10* | (2016.01) | |
| *F21Y 113/13* | (2016.01) | |

(52) U.S. Cl.
CPC .......... *A61N 5/0616* (2013.01); *F21V 23/003* (2013.01); *H01L 33/504* (2013.01); *A61L 2202/11* (2013.01); *A61L 2202/14* (2013.01); *A61N 2005/0648* (2013.01); *A61N 2005/0651* (2013.01); *A61N 2005/0659* (2013.01); *A61N 2005/0661* (2013.01); *A61N 2005/0663* (2013.01); *F21Y 2113/13* (2016.08); *F21Y 2115/10* (2016.08)

(58) Field of Classification Search
CPC .............. A61L 2202/14; A61N 5/0616; A61N 2005/0648; A61N 2005/0651; A61N 2005/0659; A61N 2005/0661; F21V 23/003; F21V 23/0435; H01L 33/504; F21Y 2113/13; F21Y 2115/10; F21W 2131/20
See application file for complete search history.

(56) References Cited

U.S. PATENT DOCUMENTS

| | | | |
|---|---|---|---|
| 2005/0177140 A1 | 8/2005 | Jay | |
| 2008/0091250 A1* | 4/2008 | Powell | H05B 45/20 607/90 |
| 2010/0287830 A1* | 11/2010 | Chen | A01G 7/045 362/1 |
| 2012/0263793 A1 | 10/2012 | Vitaliano | |
| 2013/0231719 A1 | 9/2013 | Soltesz-Nagy et al. | |
| 2013/0289132 A1 | 10/2013 | Greuel et al. | |
| 2014/0185281 A1 | 7/2014 | Lee et al. | |
| 2016/0114183 A1 | 4/2016 | Bartholomew et al. | |
| 2017/0238390 A1 | 8/2017 | Yamakawa et al. | |
| 2018/0077767 A1* | 3/2018 | Soler | H05B 45/20 |
| 2018/0117193 A1* | 5/2018 | Yadav | H05B 45/30 |
| 2018/0160504 A1 | 6/2018 | Van De Ven et al. | |
| 2018/0180226 A1 | 6/2018 | Van Bommel et al. | |
| 2018/0318599 A1 | 11/2018 | Van Bommel et al. | |
| 2019/0103523 A1 | 4/2019 | Choi et al. | |
| 2019/0139943 A1* | 5/2019 | Tiwari | F21K 9/232 |
| 2019/0373687 A1 | 12/2019 | Williams et al. | |

FOREIGN PATENT DOCUMENTS

| | | | |
|---|---|---|---|
| KR | 10-2017-0120260 | 10/2017 | |
| KR | 10-1910488 | 10/2018 | |
| WO | 2008/027438 | 3/2008 | |
| WO | 2016/007798 | 1/2016 | |
| WO | 2016007798 | 1/2016 | |
| WO | 2016/184852 | 11/2016 | |
| WO | WO-2016184852 A1 * | 11/2016 | .......... A61N 5/0618 |
| WO | 2017080807 | 5/2017 | |

OTHER PUBLICATIONS

Non-Final Office Action dated Dec. 11, 2020, in U.S. Appl. No. 16/793,329.
Final Office Action dated Apr. 12, 2021, in U.S. Appl. No. 16/793,329.
Advisory Action dated Jul. 27, 2021, in U.S. Appl. No. 16/793,329.
Non-Final Office Action dated Aug. 23, 2021, in U.S. Appl. No. 16/793,329.
Notice of Allowance dated Apr. 25, 2022, in U.S. Appl. No. 16/793,329.
European Search Report dated Oct. 24, 2022, issued to European Patent Application No. 20759129.8.
Indonesian Office Action dated Mar. 8, 2023, in Indonesian Patent Application No. P00202107477 (with English Translation).

* cited by examiner

CIE 174:2006

LED LIGHTING APPARATUS AND LIGHTING SYSTEM HAVING THE SAME

CROSS-REFERENCE TO RELATED APPLICATIONS

This application is a Continuation of U.S. patent application Ser. No. 16/793,329, filed Feb. 18, 2020, which claims the benefit of U.S. Provisional Application 62/807,333, filed Feb. 19, 2019, each of which is hereby incorporated in its entirety by reference for all purposes as set forth herein.

BACKGROUND

Field

Exemplary embodiments of the invention relate generally to a lighting apparatus and a lighting system, and more particularly, to a lighting apparatus and a lighting system using a light emitting diode as a light source.

Discussion of the Background

As an inorganic light source, light emitting diodes have been used in various fields including displays, vehicular lamps, general lighting, and the like. In particular, with various advantages such as long lifespan, low power consumption, and rapid response, light emitting diodes have been replacing existing conventional light sources.

Sunlight exhibits a broad spectrum of wavelengths in the ultraviolet, visible, and infrared regions. The human body has survived by adapting to sunlight, and accordingly, light over a broad wavelength range has been utilized.

Unlike sunlight, general lighting is mainly limited to the visible region and does provide light in a wavelength range other than visible light. As such, ordinary people living under an illumination light source cannot absorb light having a wavelength that is beneficial to the human body other than visible light. For example, it is well known that sunlight emits ultraviolet light necessary for vitamin D synthesis in the human body. However, the illumination light source does not emit ultraviolet light necessary for vitamin D synthesis, and, accordingly, people who work long hours under the illumination light source may be deficient in vitamin D.

Meanwhile, smart lighting technologies have recently been developed. For example, a user may control color temperature and brightness of a luminaire in various modes by inputting a control signal from the outside of the lighting apparatus using a remote controller, a mobile app, a personal computer(PC), or a server. However, these smart lighting technologies require a software, such as the remote controller, the mobile app, the personal computer (PC), or the server. As such, when connection between the software and the lighting apparatus is cut off due to various reasons, such as power off of the software, there is a problem in that various modes of the luminaire cannot be changed.

The above information disclosed in this Background section is only for understanding of the background of the inventive concepts, and, therefore, it may contain information that does not constitute prior art.

SUMMARY

Lighting apparatuses constructed according to exemplary embodiments of the invention are capable of providing at least one additional function together with a general lighting function, and changing at least the additional function according to time, and a lighting system having the same.

Additional features of the inventive concepts will be set forth in the description which follows, and in part will be apparent from the description, or may be learned by practice of the inventive concepts.

A lighting apparatus according to an exemplary embodiment includes: a controller including an RTC; an LED driver; and an LED luminaire, in which the LED luminaire includes a first light emitting unit emitting light for illumination, the first light emitting unit including a first light emitting diode emitting light having a peak wavelength in a range of about 300 nm to about 470 nm and a wavelength converter; and at least one of a second light emitting unit having a peak wavelength in a range of about 286 nm to about 304 nm and emitting light suitable for vitamin D production, a third light emitting unit having a peak wavelength in a range of about 605 nm to about 935 nm and emitting light suitable for producing a cell activating substance, and a fourth light emitting unit having a peak wavelength in a range of about 400 nm to about 430 nm and emitting light suitable for sterilizing pathogenic microorganisms, and the controller controls the LED driver to change irradiance of light emitted from the second light emitting unit, the third light emitting unit, or the fourth light emitting unit included in the LED luminaire according to time.

In addition to emitting light for illumination by the first light emitting unit, the lighting apparatus may emit ultraviolet light necessary for vitamin D production, light suitable for producing the cell activating substance, or light suitable for sterilizing pathogenic microorganisms, and thus, it is possible to provide the lighting apparatus providing light beneficial to the human body, similar to sunlight. Furthermore, since the lighting apparatus emits light using the light emitting diode, the lighting apparatus according to an exemplary embodiment may emit light even in an ultraviolet region, which is insufficient in sunlight, and may emit light more suitable for vitamin D production than sunlight.

Furthermore, since the controller including the RTC is placed in the lighting apparatus, it is possible for the lighting apparatus to automatically control the luminaire according to a programmed scenario without an input signal through an external input device, such as software. As such, according to seasonal time, irradiance of ultraviolet light suitable for vitamin D production, light suitable for producing the cell activating substance, or light suitable for sterilizing pathogenic microorganisms may be changed automatically according to time.

As used herein, the term sterilization may refer to killing or damaging a pathogenic microorganism to reduce or hinder the growth of the pathogenic microorganism.

In addition, the controller may drive the LED driver to change color temperature of the LED luminaire to correspond to a change in color temperature of sunlight. Accordingly, light emitting from the lighting apparatus may have a color temperature that changes in accordance to that of sunlight during one cycle.

The lighting apparatus may further include a memory storing a scenario with respect to a change in light intensity of the second light emitting unit, the third light emitting unit, or the fourth light emitting unit according to the seasonal time.

The controller may change irradiance of the second light emitting unit, the third light emitting unit, or the fourth light emitting unit according to the scenario stored in the memory.

The first light emitting unit may implement white light by the first light emitting diode and the wavelength converter.

The first light emitting diode may have a peak wavelength in a range of about 400 nm to about 430 nm. In addition, the wavelength converter may include a blue phosphor, in which the white light may have a first peak by the first light emitting diode and a second peak by the blue phosphor, the first and second peaks being located at different wavelengths from each other.

The wavelength converter may further include a green phosphor and a red phosphor.

The lighting apparatus may further include a plurality of first light emitting units, and each of the first light emitting units may implement white light while having the same or different color temperatures with each another.

The lighting apparatus may include a plurality of first light emitting units, and white light may be implemented by a combination of the first light emitting units.

The second light emitting unit may emit ultraviolet light having a peak wavelength in a range of about 291 nm to about 301 nm. Ultraviolet light in this range may synthesize vitamin D efficiently.

The second light emitting unit may be spaced apart from the wavelength converter. Light emitted from the second light emitting unit may be prevented from entering the wavelength converter, and thus, light emitted from the second light emitting unit may be prevented from being wavelength-converted. Accordingly, light loss due to the wavelength conversion of light emitted from the second light emitting unit may be prevented. Furthermore, color temperature of the lighting apparatus may be easily adjusted by preventing light emitted from the second light emitting unit from being incident on the wavelength converter and emitting the wavelength-converted light.

The cell activating substance may be nitric oxide (NO) produced by cytochrome c oxidase activity in mitochondria. NO may improve the health of the human body by affecting pain relief and improving blood circulation. Furthermore, light suitable for producing the cell activating substance may be absorbed by the intracellular mitochondria, and thus, allows the mitochondria to produce more ATPs and enhances metabolism.

The wavelength converter may include a wavelength converting substance converting a wavelength into light having a peak wavelength in a range of about 685 nm to about 705 nm, about 790 nm to about 840 nm, or about 875 nm to about 935 nm, and the LED luminaire may include the second light emitting unit or the fourth light emitting unit. When the wavelength converter emits light having the peak wavelength within the above range, the first light emitting unit may emit light suitable for producing a cell activating substance, and thus, the third light emitting unit may be omitted.

The third light emitting unit may emit light having the peak wavelength in the range of about 685 nm to about 705 nm, about 790 nm to about 840 nm, or about 875 nm to about 935 nm.

In these wavelength ranges, an energy absorption rate of cytochrome c oxidase is relatively higher. In particular, the cytochrome c oxidase exhibits the highest absorption in the range of 790 nm to 840 nm, and followed by in the range of 875 nm to 935 nm.

The peak wavelength of light emitted from the fourth light emitting unit may be the same as that of light emitted from the first light emitting diode.

The peak wavelength of light emitted from the fourth light emitting unit may be different from that of light emitted from the first light emitting diode. In particular, the peak wavelength of light emitted from the fourth light emitting unit may be about 405 nm.

The lighting apparatus may further include a circuit board on which the first light emitting unit and at least one light emitting unit of the second to third light emitting units are mounted.

A lighting system according to another exemplary embodiment includes: a lighting apparatus; and an electronic control unit to input a signal into the lighting apparatus, in which the lighting apparatus includes: a controller including an RTC; an LED driver; and an LED luminaire including a first light emitting unit emitting light for illumination, the first light emitting unit including a first light emitting diode emitting light having a peak wavelength in a range of about 300 nm to about 470 nm and a wavelength converter; and at least one of a second light emitting unit having a peak wavelength in a range of about 286 nm to about 304 nm and emitting light suitable for vitamin D production, a third light emitting unit having a peak wavelength in a range of about 605 nm to about 935 nm and emitting light suitable for producing a cell activating substance, and a fourth light emitting unit having a peak wavelength in a range of about 400 nm to about 430 nm and emitting light suitable for sterilizing pathogenic microorganisms, and the controller controls the LED driver to change irradiance of light emitted from the second light emitting unit, the third light emitting unit or the fourth light emitting unit included in the LED luminaire according to time.

The electronic control unit may include a remote controller, a mobile app, a PC or a server. The electronic control unit may be used to drive the lighting apparatus in various modes.

The electronic control unit may communicate wirelessly with the controller, and a communication module may be embedded in the lighting apparatus.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

When an element, such as a layer, is referred to as being "on," "connected to," or "coupled to" another element or layer, it may be directly on, connected to, or coupled to the other element or layer or intervening elements or layers may be present. When, however, an element or layer is referred to as being "directly on," "directly connected to," or "directly coupled to" another element or layer, there are no intervening elements or layers present. To this end, the term "connected" may refer to physical, electrical, and/or fluid connection, with or without intervening elements. Further, the D1-axis, the D2-axis, and the D3-axis are not limited to three axes of a rectangular coordinate system, such as the x, y, and z-axes, and may be interpreted in a broader sense. For example, the D1-axis, the D2-axis, and the D3-axis may be perpendicular to one another, or may represent different directions that are not perpendicular to one another. For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

Spatially relative terms, such as "beneath," "below," "under," "lower," "above," "upper," "over," "higher," "side" (e.g., as in "sidewall"), and the like, may be used herein for descriptive purposes, and, thereby, to describe one elements relationship to another element(s) as illustrated in the drawings. Spatially relative terms are intended to encompass different orientations of an apparatus in use, operation, and/or manufacture in addition to the orientation depicted in the drawings. For example, if the apparatus in the drawings is turned over, elements described as "below" or "beneath" other elements or features would then be oriented "above" the other elements or features. Thus, the exemplary term "below" can encompass both an orientation of above and below. Furthermore, the apparatus may be otherwise oriented (e.g., rotated 90 degrees or at other orientations), and, as such, the spatially relative descriptors used herein interpreted accordingly.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

Various exemplary embodiments are described herein with reference to sectional and/or exploded illustrations that are schematic illustrations of idealized exemplary embodiments and/or intermediate structures. As such, variations from the shapes of the illustrations as a result, for example, of manufacturing techniques and/or tolerances, are to be expected. Thus, exemplary embodiments disclosed herein should not necessarily be construed as limited to the particular illustrated shapes of regions, but are to include deviations in shapes that result from, for instance, manufacturing. In this manner, regions illustrated in the drawings may be schematic in nature and the shapes of these regions may not reflect actual shapes of regions of a device and, as such, are not necessarily intended to be limiting.

As is customary in the field, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts.

Further, the blocks, units, and/or modules of some exemplary embodiments may be physically combined into more complex blocks, units, and/or modules without departing from the scope of the inventive concepts.

Unless otherwise defined, all terms (including technical and scientific terms) used herein have the same meaning as commonly understood by one of ordinary skill in the art to which this disclosure is a part. Terms, such as those defined in commonly used dictionaries, should be interpreted as having a meaning that is consistent with their meaning in the context of the relevant art and should not be interpreted in an idealized or overly formal sense, unless expressly so defined herein.

Hereinafter, exemplary embodiments will be described in detail with reference to the accompanying drawings.

Figure 1:
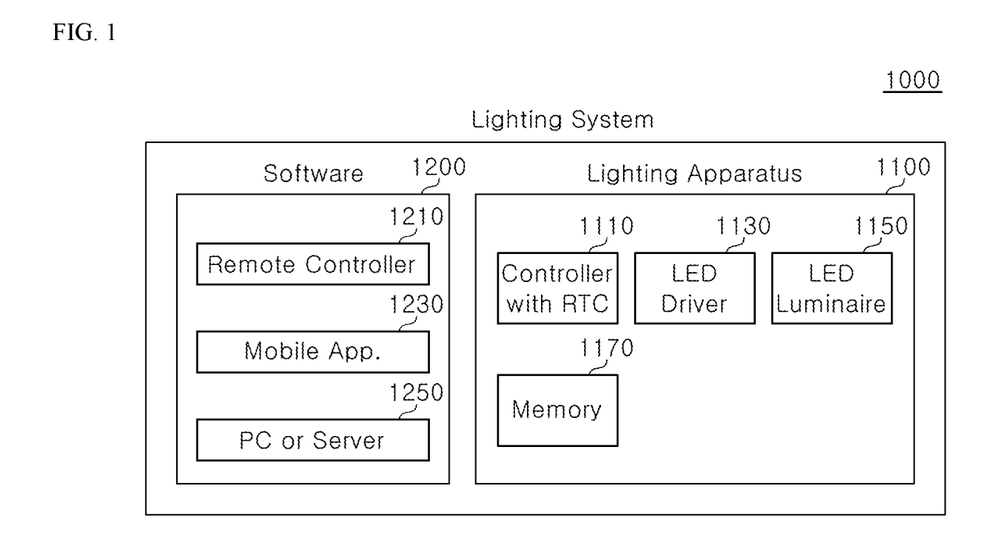
FIG. 1 is a schematic block diagram illustrating a lighting system according to an exemplary embodiment.

FIG. 1 is a schematic block diagram illustrating a lighting system according to an exemplary embodiment.

Referring to FIG. 1, the lighting system 1000 according to the illustrated exemplary embodiment may include a lighting apparatus 1100 and a software 1200 for operating the lighting apparatus 1100.

The lighting apparatus 1100 includes a controller 1110, an LED driver 1130, an LED luminaire 1150, and a memory 1170. The software 1200 may include an electronic control unit, such as a remote controller 1210, a mobile app 1230, and a personal computer or server 1250. The software 1200 and the lighting apparatus 1100 may communicate with each other through a wired or wireless communication module.

The LED luminaire 1150 includes a light emitting device having a plurality of light emitting units. The LED luminaire 1150 may include a general LED luminaire, and may implement light of various color temperatures. The LED luminaire 1150 may have an additional function in addition to a general lighting function. The additional function relates to, for example, emitting ultraviolet light for vitamin D synthesis, emitting light with a sterilizing function, or emitting red or infrared light for cell activation. To this end, the light emitting device may include a light emitting unit emitting ultraviolet light suitable for vitamin D synthesis, a light emitting unit emitting violet visible light, and/or a light emitting unit emitting infrared light. A detailed configuration of the light emitting device will be described in more detail later with reference to FIG. 3.

The software 1200 transmits a signal for operating the lighting apparatus 1100, and the controller 1110 receives the signal transmitted from the software 1200 to drive the LED driver 1130. Accordingly, the LED driver 1130 operates the light emitting units in the LED luminaire 1150 to irradiate light for illumination, and also operates the light emitting units to perform additional functions. The LED driver 1130 may drive the light emitting units by dimming using a pulse width modulation method.

In addition, the software 1200 may transmit a signal to change a mode of the LED luminaire 1150. For example, the software 1200 may set a mode, in which the LED luminaire 1150 changes color temperature or performs additional functions according to the change of sunlight, or may set a user-specified mode for a change in color temperature and a change in additional function according to time.

For example, the remote controller 1210 transmits an input signal, and the controller 1110 receiving the signal through a wireless communication module may drive the LED driver 1130 according to a mode, which is set according to the input signal of the remote controller 1210. The signal may be transmitted through the mobile app 1230, or may be transmitted through the PC or the server 1250.

When the user inputs the control signal using the remote controller 1210, the mobile app 1230, the server 1250, or the like from the outside of the lighting apparatus 1100 to adjust color temperature and brightness of the LED luminaire 1150, the user may set the mode for adjusting color temperature and brightness of the LED luminaire 1150, or for adjusting additional functions of the LED luminaire 1150.

While the mode of the LED luminaire 1150 may be changed through the software 1200, in some exemplary embodiments, the user may directly change various modes of the LED luminaire 1150 by adjusting a switch connected to the controller 1110 by a wire, or a sensor may be installed in the LED luminaire 1150 to change the mode of the LED luminaire 1150 through the sensor.

The controller 1110 includes a real time clock (RTC). The RTC may be included in the controller 1110 in a form of an integrated circuit. Since the controller 1110 includes the RTC, the controller 1110 may control the LED luminaire 1150 according to a schedule without receiving the signal from the outside according to the set mode.

For example, color temperature and brightness of sunlight according to seasonal time, intensity of ultraviolet light, intensity of infrared light, or the like may be stored in the memory 1170, and the controller 1110 may control the light emitting device in the LED luminaire 1150 to emit light similar to sunlight according to the seasonal time using the RTC. Accordingly, the LED luminaire 1150 may illuminate an interior space while changing the spectrum of light emitted from the light emitting device according to the spectrum change of sunlight during the daytime.

The memory 1170 may also store a scenario, such as color temperature and brightness of sunlight, intensity of ultraviolet light, and intensity of infrared light according to a predetermined time, and the controller 110 may control the light emitting device in the LED luminaire 1150 using the RTC according to the scenario stored in the memory 1170.

Figure 2:
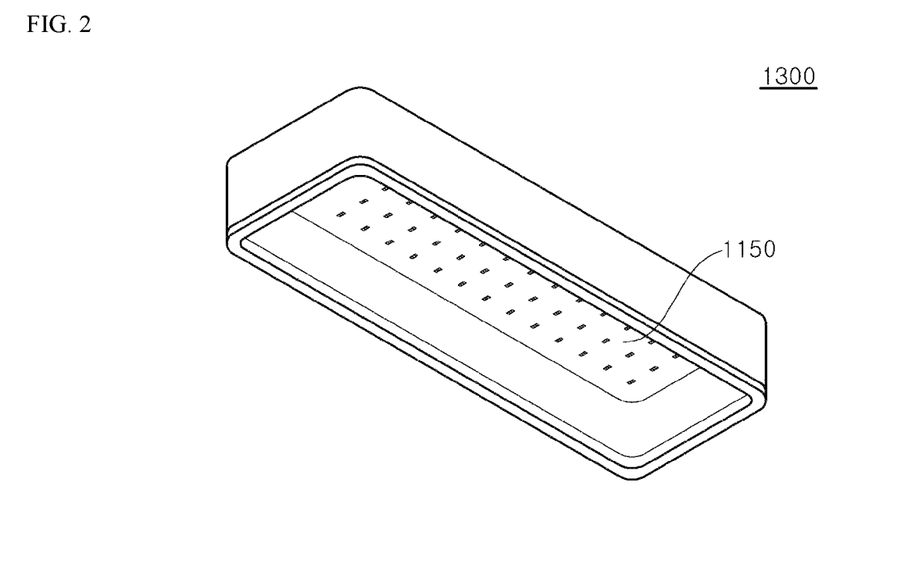
FIG. 2 is a schematic perspective view illustrating a lighting apparatus according to an exemplary embodiment.
Figure 3:
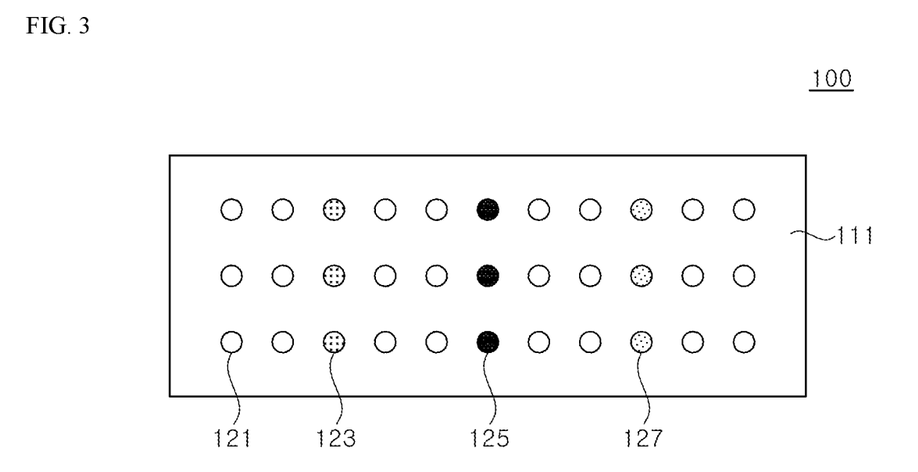
FIG. 3 is a schematic plan view illustrating a light emitting device according to an exemplary embodiment.
Figure 4:
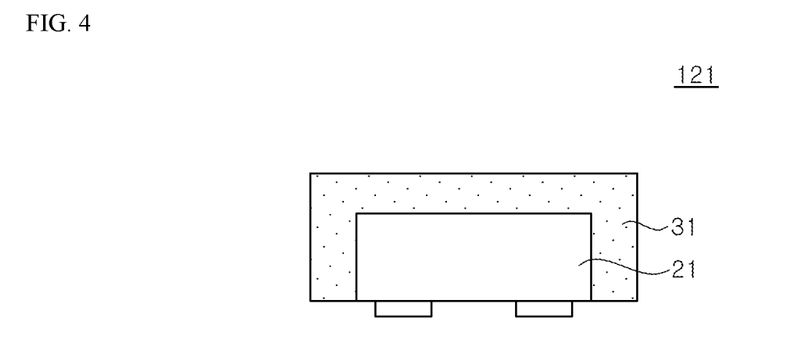
FIG. 4 is a schematic cross-sectional view illustrating a light emitting unit according to an exemplary embodiment.

FIG. 2 is a schematic perspective view illustrating a lighting apparatus according to an exemplary embodiment, FIG. 3 is a schematic plan view illustrating a light emitting device according to an exemplary embodiment, and FIG. 4 is a schematic cross-sectional view illustrating a light emitting unit according to an exemplary embodiment.

Referring to FIG. 2, the lighting apparatus 1300 has an LED luminaire 1150. The LED luminaire 1150 defines an appearance of lighting apparatus 1300. The LED luminaire 1150 may be a panel luminaire, but is not limited thereto, and may be a tube or lamp luminaire in some exemplary embodiments. The lighting apparatus 1300 may be used for general home use or for office use. The controller 1110, the LED driver 1130, and the memory 1170 described with reference to FIG. 1 may be mounted inside the LED luminaire 1150.

The LED luminaire 1150 includes a light emitting device 100 shown in FIG. 3. The light emitting device 100 may include light emitting units 121, 123, 125, and 127 mounted on a circuit board 111. Each of the light emitting units 121, 123, 125, and 127 may include a light emitting diode, and a configuration of each of the light emitting units will be described in detail later.

The circuit board 111 may have a circuit pattern for supplying power to the first to fourth light emitting units 121, 123, 125, and 127. The circuit board 111 may be a printed circuit board, for example, a metal-PCB. The circuit board 111 and the first to fourth light emitting units 121, 123, 125, and 127 mounted thereon may be disposed in the lighting apparatus 1300 as a light emitting module.

At least one first light emitting unit 121 may be mounted on the circuit board 111, as a light source for implementing white light. As illustrated in FIG. 4, the first light emitting unit 121 may include a first light emitting diode 21 and a wavelength converter 31. The first light emitting diode 21 is, for example, an inorganic light emitting diode formed using a group III nitride semiconductor, such as an AlGaInN-based semiconductor, without being limited thereto. The first light emitting diode 21 may be a light emitting diode chip well-known in the art, and it is not limited to a particular structure, such as a flip chip type, a vertical type, or a lateral type.

A plurality of first light emitting diodes 21 may be electrically connected to one another in various ways, for example, may be connected in series, in parallel, or in series-parallel. The plurality of first light emitting diodes 21 may be disposed in various ways according to the lighting apparatus. For example, the plurality of first light emitting diodes 21 may be disposed in two dimensions for a surface lighting apparatus, or the first light emitting diodes 21 may be disposed along a line for a tubular lighting apparatus.

The first light emitting diode 21 may emit ultraviolet light or visible light, and may emit light have a peak wavelength in a range of about 300 nm to about 470 nm, for example. In particular, the first light emitting diode 21 may have a peak wavelength in a range of about 400 nm to about 430 nm. When the first light emitting diode 21 emits ultraviolet light, most of the ultraviolet light is wavelength-converted by the wavelength converter 31, thereby preventing the ultraviolet light from being emitted from the first light emitting diode 21 to the outside. Furthermore, when the first light emitting diode 21 emits light having the peak wavelength in the range of 400 nm to 430 nm, the safety problem that may be caused by ultraviolet light may be eliminated in advance. Furthermore, when using the first light emitting diode emitting light having the peak wavelength in the range of about 400 nm to about 430 nm, the energy loss due to the wavelength conversion may be reduced compared to the ultraviolet light, and eye diseases or skin diseases caused by blue light may be prevented. This will be described in more detail later with reference to FIG. 5.

The wavelength converter 31 converts a wavelength of light emitted from the first light emitting diode 21. The wavelength converter 31 may be, for example, a resin layer including a phosphor or a quantum dot. Each of the wavelength converters 31 may cover the first light emitting diodes 21, without being limited thereto. In some exemplary embodiments, a single wavelength converter 31 may cover each of the plurality of first light emitting diodes 21.

The wavelength converter 31 includes a wavelength converting substance for implementing white light together with light from the first light emitting diode 21. In one exemplary embodiment, the wavelength converter 31 may include a blue phosphor, a green phosphor, and a red phosphor. In another exemplary embodiment, the wavelength converter 31 may include a blue phosphor and an orange phosphor. In another exemplary embodiment, when the first light emitting diode 21 is a blue light emitting diode, the wavelength converter 31, without a blue phosphor, may include a green phosphor and a red phosphor or an orange phosphor. In another exemplary embodiment, the wavelength converter 31 may include quantum dots instead of, or in addition to the phosphor.

Blue phosphor may include a BAM-based, a halo-phosphate-based, or an aluminate-based phosphor, and may include, for example, $BaMgAl_{10}O_{17}:Mn^{2+}$, $BaMgAl_{12}O_{19}:Mn^{2+}$ or $(Sr,Ca,Ba)PO_4Cl:Eu^{2+}$. The blue phosphor may have, for example, a peak wavelength in a range of 440 nm to 500 nm.

Green phosphor may include $LuAG(Lu_3(Al,Gd)_5O_{12}:Ce^{3+})$, $YAG(Y_3(Al,Gd)_5O_{12}:Ce^{3+})$, Ga—$LuAG((Lu,Ga)_3(Al,Gd)_5O_{12}:Ce^{3+})$, Ga—YAG $((Ga,Y)_3(Al,Gd)_5O_{12}:Ce^{3+})$, LuYAG $((Lu,Y)_3(Al,Gd)_5O_{12}:Ce^{3+})$, ortho-silicate $((Sr,Ba,Ca,Mg)_2SiO_4:Eu^{2+})$, oxynitride $((Ba,Sr,Ca)Si_2O_2N_2:Eu^{2+})$, β-SiAlON:$Eu^{2+}$, Ca-α-SiAlON:$Eu^{2+}$, or thio gallate $(SrGa_2S_4:Eu^{2+})$. The green phosphor may have a peak wavelength is in a range of 500 nm to 600 nm.

Red phosphor may include a nitride-based, a sulfide-based, a fluoride or an oxynitride-based phosphor, and, specifically, may include $CASN(CaAlSiN_3:Eu^{2+})$, $(Ba,Sr,Ca)_2Si_5N_8:Eu^{2+}$, $(Ca,Sr)S_2:Eu^{2+}$, or $(Sr,Ca)_2SiS_4:Eu^{2+}$. The red phosphor may have a peak wavelength in a range of 600 nm to 700 nm.

White light having various color temperatures may be implemented by a combination of the first light emitting diode 21 and the wavelength converter 31.

Figure 5:
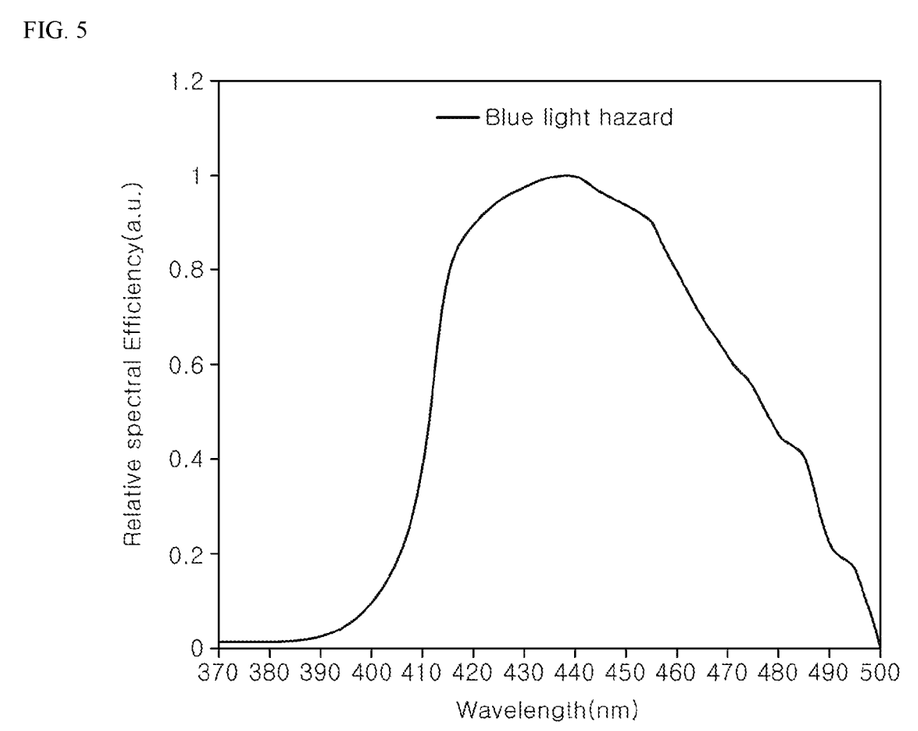
FIG. 5 is a graph showing a degree of hazard according to wavelengths of blue light.

Meanwhile, as described above, blue light is known to cause the eye diseases and skin diseases. FIG. 5 is a graph showing a degree of hazard according to wavelengths of blue light.

Referring to FIG. 5, the highest degree of hazard is exhibited in a wavelength range between 430 nm and 440 nm. A wavelength range of 420 nm to 455 nm exhibits 90% or more degree of hazard based on the highest hazard value, and a wavelength rage of 413 nm to 465 nm exhibits 70% or more degree of hazard, and a wavelength range of 411 nm to 476 nm exhibits 50% or more degree of hazard. Meanwhile, ultraviolet light harms the human body and, in particular, exhibits the highest degree of hazard between 270 nm and 280 nm.

Figure 6:
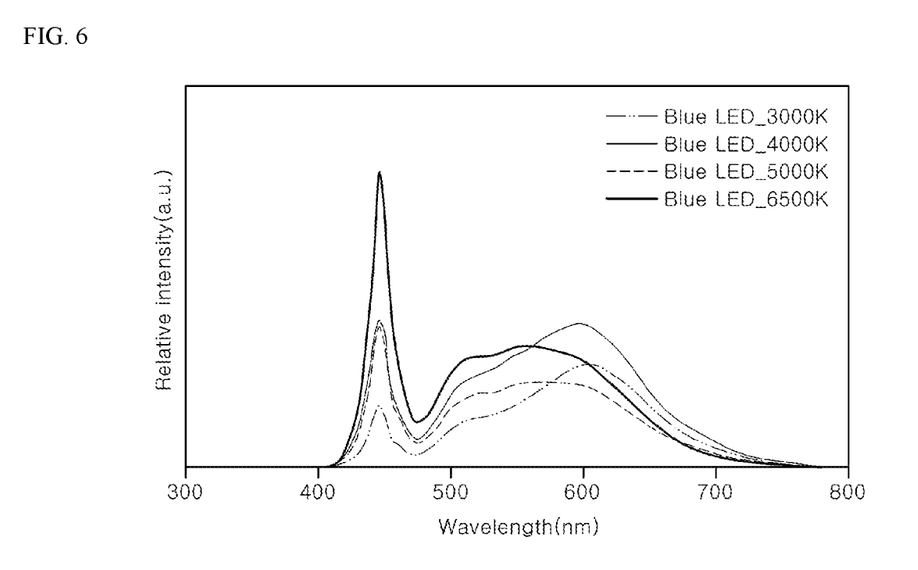
FIG. 6 shows a spectrum of a white light source using a general blue light emitting diode.

FIG. 6 shows a spectrum of a white light source using a general blue light emitting diode 21.

Referring to FIG. 6, in general, the white light source may implement white light using a yellow phosphor, or a green phosphor and a red phosphor, together with the blue light emitting diode. A type of phosphor and an amount of phosphor are controlled according to a color temperature, and an intensity of the blue light increases as color temperature increases.

The blue light emitting diode used in the white light source generally has a peak wavelength in a range of about 430 nm to about 470 nm. Blue light in this range has a relatively high degree of hazard as shown in FIG. 5. Therefore, as the color temperature of the white light source increases, the intensity of the blue light increases, thereby increasing the hazard of causing the eye diseases or skin diseases.

Figure 7:
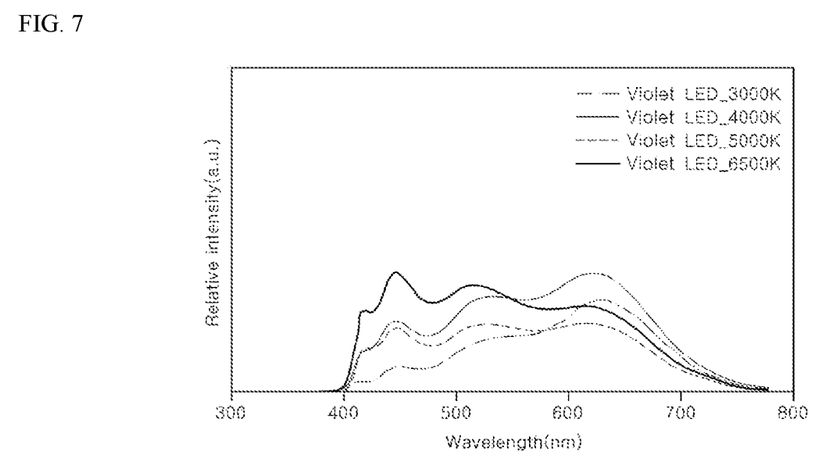
FIG. 7 illustrates spectra of white light sources according to exemplary embodiments.

Meanwhile, FIG. 7 illustrates spectra of white light sources according to exemplary embodiments. In particular, FIG. 7 exemplarily shows the spectrum of white light of various color temperatures implemented by a combination of a violet light emitting diode 21 and a wavelength converter 31.

Referring to FIG. 7, white light of each color temperature is implemented by a combination of light emitted from phosphors and light emitted from the violet light emitting diode 21 having a peak wavelength in a range of about 400 nm to about 430 nm.

In this case, the wavelength converter 31 includes a blue phosphor, and further includes a green phosphor and a red phosphor. These phosphors absorb light emitted from the violet light emitting diode 21 and emit blue light, green light, and red light.

White light of various color temperatures shown in FIG. 7 has a peak due to the violet light emitting diode 21 and a peak due to the blue phosphor. These peaks are especially distinct as the color temperature becomes higher. The peak due to the violet light emitting diode 21 and the peak due to the blue phosphor are located at different wavelengths from each other. In particular, since the blue phosphor converts a wavelength of light emitted from the violet light emitting diode 21 into a longer wavelength, the peak by the blue phosphor is located at a longer wavelength than that of the peak by the violet light emitting diode 21.

In addition, irradiance of light emitted from the light emitting diode 21 at all color temperatures may be less than that of light emitted from the blue phosphor. As the color temperature increases, although the irradiance of light emitted from the light emitting diode 21 also increases, irradiance of blue light emitted from the blue phosphor increases to a greater extent. In addition, the irradiance of light emitted from the light emitting diode 21 may be less than that of light emitted from the green phosphor, and may be less than that of light emitted from the red phosphor.

Accordingly, the lighting apparatus may further prevent the occurrence of eye diseases or skin diseases caused by light emitted from the first light emitting diode 21. However, as described above, since the wavelength in about 400 nm to about 430 nm range has a relatively low hazard to the human body, the irradiance thereof may be further increased.

Further, light emitted from the light emitting diode 21 having the peak wavelength in the range of about 400 nm to about 430 nm may have a sterilizing function. As such, the light emitting diode 21 may emit light having a peak wavelength of about 400 nm to about 410 nm, and more particularly, a peak wavelength of about 405 nm. Short wavelength visible light in the range of about 400 nm to about 430 nm has a relatively low hazard to eye diseases or skin diseases, and has a high sterilizing capacity against pathogenic microorganisms, and thus, the short wavelength visible light may be suitably used for the lighting apparatus to perform the sterilizing function.

Referring back to FIG. 3, the second light emitting unit 123 may include an ultraviolet light emitting diode emitting ultraviolet light of UVB. The ultraviolet light emitting diode may emit light having a peak wavelength, specifically in a range of about 286 nm to about 304 nm, more specifically in a range of about 291 nm to about 301 nm. When ultraviolet light in this range is irradiated to the human body, vitamin D may be efficiently synthesized. The ultraviolet light emitting diode is, for example, an inorganic light emitting diode formed using a group III nitride semiconductor, without being limited thereto. The ultraviolet light emitting diode may be a light emitting diode chip well-known in the art, and is not limited to a particular structure, such as a flip chip type, a vertical type or a horizontal type.

The ultraviolet light emitting diode of the second light emitting unit 123, unlike the first light emitting unit 121, may not include a wavelength converter for converting a wavelength of light emitted from the ultraviolet light emitting diode. The second light emitting unit 123 may be spaced apart from the wavelength converter 31 of the first light emitting unit 121, and thus, light emitted from the ultraviolet light emitting diode may be prevented from being absorbed by the wavelength converter 31. Accordingly, irradiance of light emitted from the second light emitting unit 123 may be improved. Furthermore, the second light emitting unit 123 is spaced apart from the wavelength converter 31, and thus, it is possible to prevent wavelength conversion of light emitted from the ultraviolet light emitting diode, thereby preventing energy loss due to the stoke shift. However, the inventive concepts are not limited thereto, and in some exemplary embodiments, the second light emitting unit 123 may include a wavelength converter, or may be disposed in the wavelength converter 31 of the first light emitting unit 121.

Figure 8:
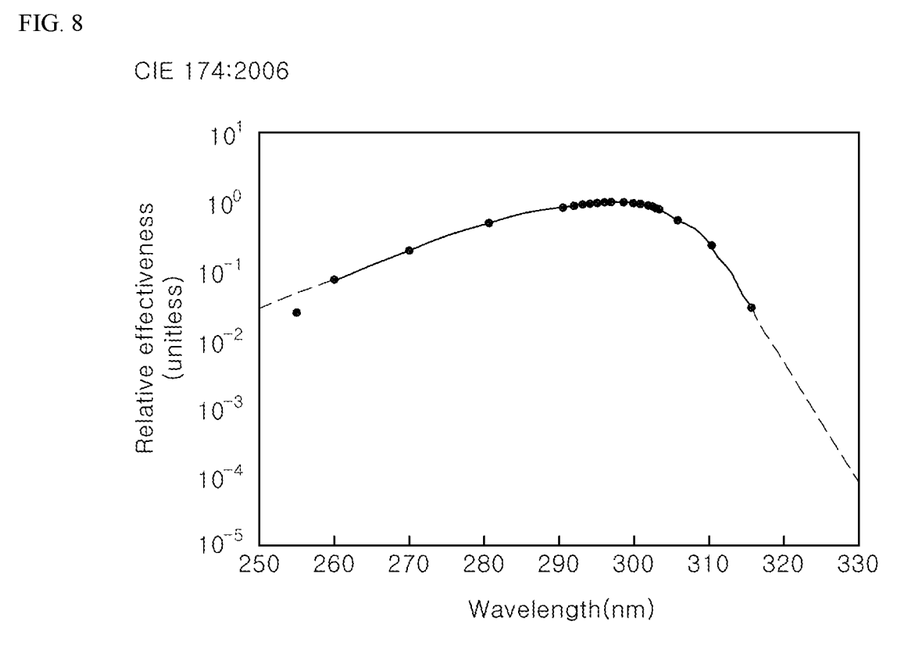
FIG. 8 is a graph showing effectiveness of vitamin D production in the human body according to wavelengths.

Meanwhile, ultraviolet light emitted to the outside may be used for the synthesis of vitamin D. It is well-known in the art that 7-dehydrocholesterol in skin cells reacts with UVB to synthesize Cholecalciferol (vitamin D3). FIG. 8 is a graph showing effectiveness of vitamin D production in the human body according to wavelengths, as published in CIE 174: 2006.

Referring to FIG. 8, ultraviolet light having a wavelength of 298 nm is most efficient for vitamin D production, and a wavelength in a range of about 291 nm to about 301 nm is exhibits an efficiency of about 90% or more, compared to the highest efficiency. In addition, ultraviolet light having a wavelength in a range of about 286 nm to about 304 nm exhibits about 70% or more efficiency compared to the highest efficiency, and a wavelength in a range of about 281 nm to about 306 nm exhibits about 50% or more efficiency compared to the highest efficiency. When a peak wavelength of the light emitting diode 23 is 298 nm, it is most efficient for vitamin D production, and, when is within the range of about 286 nm to about 304 nm, it will exhibit a relatively favorable efficiency of 70% or more for vitamin D production.

Vitamin D is involved in calcium metabolism, and a deficiency of vitamin D causes a major impediment to bone growth. Although a recommended daily dose of vitamin D varies from country to country, daily dosage to maintain an adequate level of vitamin D is generally suggested to be in a range of 400 IU to 800 IU, and has been adjusted upward. For example, the International Commission on Illumination (CIE) suggests the UVB exposure required to produce 1000 IU of vitamin D, which is about 21 $J/m^2$ to about 34 $J/m^2$, for the entire body of the second skin type based on the sunlight at noon in midsummer. Meanwhile, a reference dose for the human exposure safety range for UVB provided by the American Conference of Governmental Industrial Hygienists (ACGIH) is 47 $J/m^2$ for 290 nm, about 65 $J/m^2$ for 297 nm, and 100 $J/m^2$ for 300 nm.

As such, a dose of UVB irradiated by the lighting apparatus may be adjusted, so that it may be used for vitamin D synthesis in a range not exceeding the safety range. Because a daily permissible reference dose increases as the wavelength increases even in the ultraviolet region of UVB, the peak wavelength of the second light emitting diode 23 may be irradiated with more ultraviolet light having a wavelength of 298 nm or longer, for example, 298 nm to 301 nm, and thus, it is more suitable for the lighting apparatus having the vitamin D synthesis function.

The second light emitting unit 123 may be driven independently from the first light emitting unit 121, and thus, may be turned on or off as needed while the first light emitting unit 121 is operating. In particular, as described with reference to FIG. 1, an intensity of ultraviolet light emitted from the first light emitting unit 121 may be automatically adjusted according to time by the controller 1110 including the RTC. For example, the second light emitting unit 123 may irradiate ultraviolet light in response to a change of the ultraviolet light intensity in sunlight during a day, or may automatically change the ultraviolet light intensity according to a value preset by a user without external input.

A third light emitting unit 125 emits red light or infrared light suitable for cell activation. The third light emitting unit 125 may be mounted on the circuit board 111 spaced apart from the wavelength converter 31 of the first light emitting unit 121. Light emitted from the third light emitting unit 125 may be emitted to the outside without substantially entering the wavelength converter 31. Accordingly, light emitted from the third light emitting unit 125 may be prevented from being absorbed by the wavelength converter 31.

The third light emitting unit 125 may include, for example, a light emitting diode formed of an AlGaInP-based or AlGaInAs-based semiconductor. In this case, the third light emitting unit 125 may emit light of a desired wavelength without a separate wavelength converter. In another exemplary embodiment, the third light emitting unit 125 may include a light emitting diode formed of an AlGaInN-based semiconductor, and a wavelength converter for converting wavelengths into red light or infrared light. For example, the AlGaInN-based light emitting diode may emit ultraviolet light or blue light, and the wavelength converter may convert ultraviolet light or blue light into red light or infrared light. In this case, the wavelength converter may include the red phosphor or the quantum dot as described above. In particular, quantum dots may convert ultraviolet light or blue light into red or infrared light having a narrow half-width, and thus, it is suitable for emitting light of a specific target wavelength.

The third light emitting unit 125 may be connected in series or in parallel to the first light emitting unit 121, or may be driven independently from the first light emitting unit 121.

Light suitable for cell activation has a peak wavelength, for example, in a range of about 605 nm to about 935 nm. Red light or near infrared light in the range of about 605 nm to about 935 nm produces a cell activating substance in the mitochondria. More particularly, the cytochrome c oxidase in the mitochondria absorbs light in the range of 605 nm to 935 nm as a photoreceptor to increase its activity, and, accordingly, produces nitric oxide (NO). NO improves human health by affecting pain relief and improving blood circulation. In addition, the activity of the cytochrome c oxidase protein contributes to ATP production, and also affects cell damage treatment.

Figure 9:
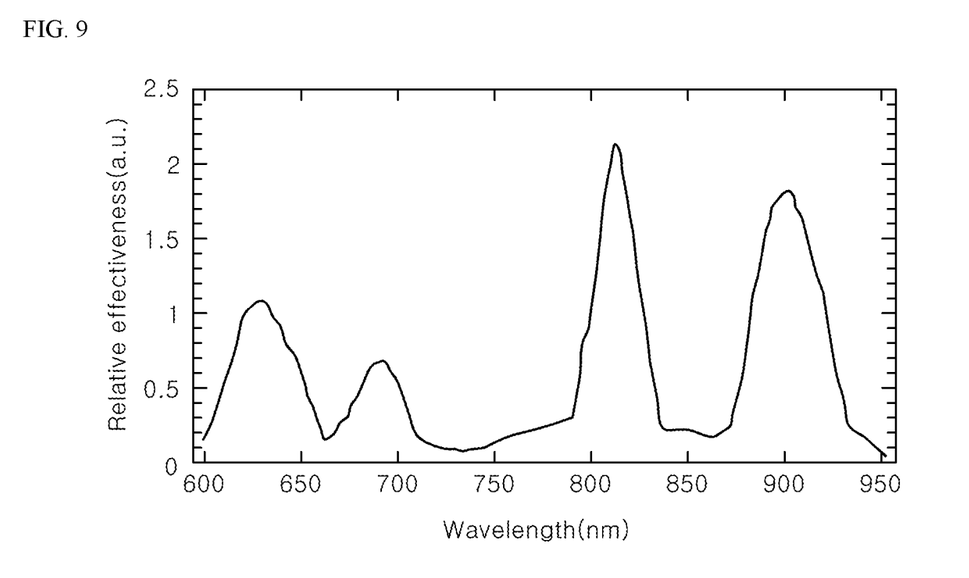
FIG. 9 is a graph showing effectiveness of cell function activity according to wavelengths.

In particular, the third light emitting unit 125 may emit light having a peak wavelength in a range of about 605 nm to about 655 nm, about 685 nm to about 705 nm, about 790 nm to about 840 nm, or about 875 nm to about 935 nm. In this range, the energy absorption rate of cytochrome c oxidase is relatively high. More particularly, the energy absorption rate of cytochrome c oxidase, as shown in FIG. 9, exhibits the highest absorption in the range of 790 nm to 840 nm, followed by the range of about 875 nm to about 935 nm, and then the range of about 605 nm to about 655 nm.

In this manner, the light emitting diode or the wavelength converter emits light having a wavelength that causes high energy absorption of cytochrome c oxidase, and thus, the efficiency of health promotion may be improved.

Further, when a plurality of third light emitting units 125 are used, light emitting diodes emitting light in a specific wavelength range described above, for example, in the range of 790 nm to 840 nm, or 875 nm to 935 nm having the high efficiency may be used in plural, and various light emitting diodes may be used to evenly emit light in each wavelength range.

In addition, when the third light emitting unit 125 emits light in the range of 605 nm to 655 nm, it may affect color temperature of white light emitted from the first light emitting units 121. In this case, color temperature of light emitted from the lighting apparatus is controlled by controlling light emitting from each of the first light emitting unit 121 and the third light emitting unit 125. Meanwhile, not to affect color temperature of the lighting apparatus, the third light emitting units 125 emitting light having a peak wavelength in a low visibility range, such as in the range of about 685 nm to about 705 nm, about 790 nm to about 840 nm, or about 875 nm to about 935 nm may be mainly used.

In the illustrated exemplary embodiment, to add a cell activating function to the lighting apparatus, irradiance of light emitted from the third light emitting unit 125 may be greater than that from the first light emitting units 121 implementing white light at the same wavelength. As such, in the illustrated exemplary embodiment, the cell activating function is mainly performed by the third light emitting unit 125.

Although a driving time of the third light emitting unit 125 and that of the first light emitting unit 121 may be the same, the inventive concepts are not limited thereto. In some exemplary embodiments, the driving time of the third light emitting unit 125 may be adjusted according to an installation location of the lighting apparatus. Furthermore, irradiance of light emitted from the third light emitting unit 125 may be automatically adjusted according to time by the controller 1110, as described above with reference to FIG. 1.

A use time or the amount of irradiance of the third light emitting unit 125 may be adjusted in consideration of the risk to the human body. For example, irradiance of the third light emitting unit 125 emitted from the lighting apparatus may be 570 W/m$^2$ or less, and further, may be 100 W/m$^2$ or less. 570 W/m$^2$ represents a limit value of risk group 1 for light in the infrared range in the Photobiological Safety Standard (IEC 62471), and 100 W/m$^2$ corresponds to an exempt. The lighting apparatus has the radiance of 570 W/m$^2$ or less, and thus, the lighting apparatus may be driven to produce a cell activating substance without harming the human body for a relatively long period of time.

The lighting apparatus according to an exemplary embodiment may be used to promote the health of the human body not only in the indoor living space but also in a space where a large number of people are active, such as an airport or a hospital.

A fourth light emitting unit 127 emits light suitable for sterilizing pathogenic microorganisms. The fourth light emitting unit 127 may be mounted on the circuit board 111 and be spaced apart from the wavelength converter 31 of the first light emitting unit 121. Light emitted from the fourth light emitting unit 127 may be emitted to the outside without actually entering the wavelength converter 31. Accordingly, irradiance of light emitted from the fourth light emitting unit 127 may be improved.

The fourth light emitting unit 127 may be connected to the first light emitting unit 121 in series or in parallel, or may be driven independently from the first light emitting unit 121.

The fourth light emitting unit 127 may include, for example, a light emitting diode that emits light having a peak wavelength of about 400 nm to about 430 nm, a peak wavelength of about 400 nm to about 410 nm, or more particularly, a peak wavelength of about 405 nm. The wavelength of about 405 nm is absorbed by porphyrin, a substance present in the cells of bacteria, to generate reactive oxygens. The generated reactive oxygens may be accumulated to destroy cell walls, thereby causing sterilization. As such, the wavelength in the visible range described above is suitable for sterilizing pathogenic microorganisms without causing eye diseases or skin diseases.

Although the light emitting diode of the fourth light emitting unit 127 may emit light having the same wavelength as that of the first light emitting unit 121, the inventive concepts are not limited thereto, and in some exemplary embodiments, the light emitting diode of the fourth light emitting unit 127 may emit light having a wavelength different from that of the first light emitting unit 121. In particular, unlike the first light emitting unit 121, the fourth light emitting unit 127 may not include a wavelength converter. The fourth light emitting unit 127 is disposed separately from the first light emitting unit 121, and thus, the sterilizing function may be efficiently provided. However, when the first light emitting unit 121 emits light suitable for the sterilizing function in some exemplary embodiments, the fourth light emitting unit 127 may be omitted.

In order to add the sterilizing function to the lighting apparatus according to the illustrated exemplary embodiment, irradiance of light emitted from the fourth light emitting unit 127 may be greater than that of the first light emitting unit 121 at the same wavelength. Furthermore, irradiance of light emitted from the fourth light emitting unit 127 may be greater than that of light emitted from the first light emitting unit 121 to the outside of the lighting apparatus. Accordingly, in the lighting apparatus according to the illustrated exemplary embodiment, the sterilizing function is mainly performed by the fourth light emitting unit 127 as compared with the first light emitting unit 121.

Although a driving time of the fourth light emitting unit 127 and that of the first light emitting unit 121 may be the same, the inventive concepts are not limited thereto. In some exemplary embodiments, the driving time of the fourth light emitting unit 127 may be adjusted according to an installation location of the lighting apparatus. In particular, a use time or the amount of irradiance of the fourth light emitting unit 127 may be adjusted in consideration of the risk to the human body.

For example, irradiance of the fourth light emitting unit 127 emitted from the lighting apparatus may be 1 $W/m^2$ or less, and in some exemplary embodiments, may be 0.1 $W/m^2$ or less. 1 $W/m^2$ represents a limit value of risk group 1 for blue light in a range 300 nm to 700 nm in the Photobiological Safety Standard (IEC 62471), and 0.1 $W/m^2$ corresponds to an exempt. The lighting apparatus has the radiance of 1 $W/m^2$ or less, and thus the lighting apparatus may be driven to sterilize for a relatively long period of time in the lighting apparatus.

According to an exemplary embodiment, pathogenic microorganisms may be sterilized not only in the indoor living space but also in a space where a large number of people work, such as an airport or a hospital, thereby preventing human infection by pathogenic microorganisms.

In the illustrated exemplary embodiment, at least one of the first to fourth light emitting units 121, 123, 125, and 127 may be disposed on the circuit board 111, respectively. In particular, the first light emitting unit 121 may be disposed more than other light emitting units in consideration of the intensity of light for illumination.

Although the light emitting device has been described as including each of the first to fourth light emitting units 121, 123, 125, and 127 disposed on the circuit board 111, however, the inventive concepts are not limited thereto. For example, a light emitting unit according to another exemplary embodiment may perform at least one additional function together with the illumination function by the first light emitting unit 121, and, in this case, one or two of the second to fourth light emitting units 123, 125, and 127 may be omitted. For example, the first and second light emitting units 121 and 123, the first and third light emitting units 121 and 125, or the first and fourth light emitting units 121 and 127 may be disposed on the circuit board 111, or the first to third light emitting units 121, 123, and 125, the first, the second, and the fourth light emitting units 121, 123, and 127, or the first, the third, and the fourth light emitting units 121, 125, and 127 may be disposed on the circuit board 111.

In addition, although the light emitting units of the same kind are illustrated as being disposed in the same row, the inventive concepts are not limited thereto. For example, in some exemplary embodiments, the same kind of light emitting units may be arranged to be spaced apart from each other.

In an exemplary embodiment, when the first light emitting unit 121 is used as a light source for illumination and emits light suitable for the sterilizing function, the fourth light emitting unit 127 may be omitted. In addition, when the first light emitting unit 121 includes a phosphor or a quantum dot for emitting light suitable for cell activation while being used as the light source for illumination, the third light emitting unit 125 may be omitted. Further, when the first light emitting unit 121 emits ultraviolet light suitable for the synthesis of vitamin D while being used as the light source for illumination, the second light emitting unit 123 may be omitted.

Further, each of the first light emitting units 121 is described as emitting white light, but the inventive concepts are not limited thereto. In some exemplary embodiments, a plurality of first light emitting units 121 may be combined to implement white light. For example, the first light emitting units 121 may include light emitting units having a high color temperature and light emitting units having a low color temperature, and color temperature of the lighting apparatus may be adjusted by adjusting light emitted from these light emitting units. In addition, in other exemplary embodiments, an individual first light emitting unit 121 may not implement white light, but white light may be implemented by a combination of at least two first light emitting units 121.

Driving of the first to fourth light emitting units 121, 123, 125, and 127 may be controlled according to time using the controller including the RTC as described with reference to FIG. 1, and information necessary for the control may be stored in the memory 1170. For example, the memory 1170 may store a spectral distribution of sunlight according to time during the seasonal day, and the controller 1110 may drive the first to fourth light emitting units 121, 123, 125, and 127 to implement light corresponding to the spectral distribution according to the seasonal time of sunlight stored in the memory 1170. In another exemplary embodiment, a user may preset the spectral distribution according to the seasonal time, and the controller 1110 may drive the first to fourth light emitting units 121, 123, 125, and 127 according to the set spectrum distribution change.

Figure 10:
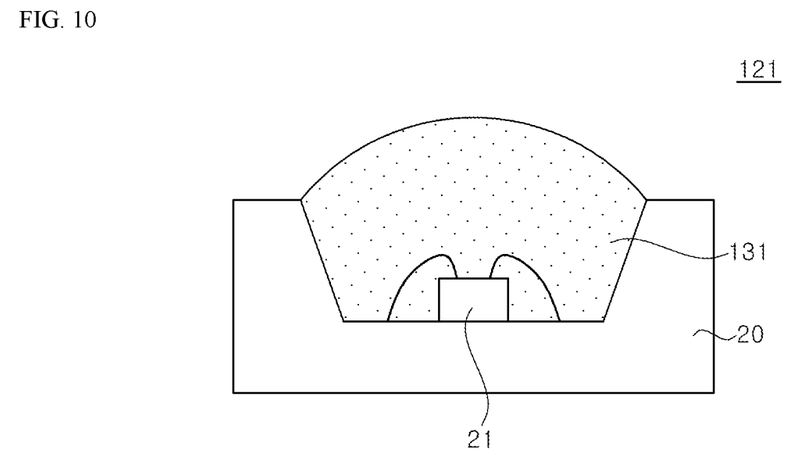
FIG. 10 is a schematic cross-sectional view illustrating a light emitting unit according to another exemplary embodiment.

FIG. 10 is a schematic cross-sectional view illustrating a light emitting unit 121 according to another exemplary embodiment. FIG. 10 schematically shows the light emitting unit 121 in a package form.

Referring to FIG. 10, the light emitting unit 121 includes a light emitting diode 21 and a wavelength converter 131. The light emitting diode 21 may be mounted in a cavity of a housing 20, and the wavelength converter 131 covers the light emitting diode 21 in the cavity. The light emitting diode 21 may be electrically connected to lead electrodes through bonding wires.

The package form of the light emitting unit 121 shown in FIG. 10 is exemplarily, and in other exemplary embodiments, various kinds of packages may be used. In addition, the wavelength converter 131 may cover the light emitting diode 21 in various shapes.

The second light emitting unit 123, the third light emitting unit 125, and the fourth light emitting unit 127 may also be provided in the form of the package, as in the first light emitting unit 121, and mounted on the circuit board 111. However, these light emitting units 123, 125, and 127 may not include the wavelength converter 131.

Figure 11:
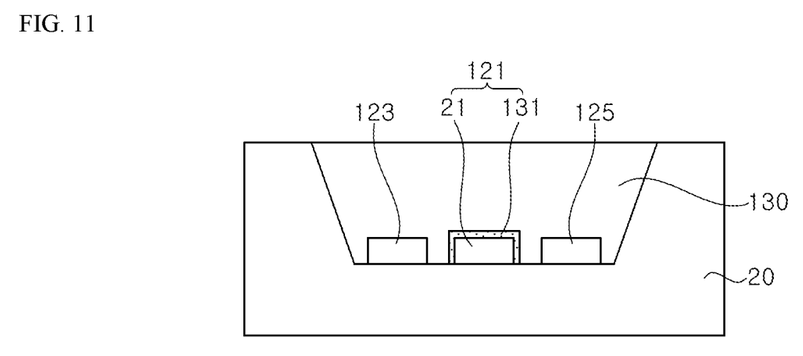
FIG. 11 is a schematic plan view illustrating a light emitting unit according to another exemplary embodiment.

FIG. 11 is a schematic plan view illustrating a light emitting unit according to another exemplary embodiment.

Referring to FIG. 11, in the light emitting unit according to the illustrated exemplary embodiment, the first light emitting unit 121, the second light emitting unit 123, and the third light emitting unit 125 may be collectively mounted as a single package. More particularly, the light emitting diode package of FIG. 10 includes a single light emitting diode, however, the light emitting diode package according to the illustrated exemplary embodiment includes at least one of the second and third light emitting units 123 and 125 together with the first light emitting unit 121.

A molding member 130 may fill a cavity to cover the light emitting units 121, 123, and 125. The molding member 130 may be formed of, for example, a transparent resin, such as silicone resin, or transparent glass. In some exemplary embodiments, the molding member 130 may include a wavelength converting substance.

According to the illustrated exemplary embodiment, the light emitting diode package including the first to third light emitting units may be mounted on the circuit board 111. In some exemplary embodiments, the light emitting diode package may further include the fourth light emitting unit 127 described above.

A plurality of light emitting diode packages may be mounted on the circuit board 111, and these light emitting diode packages may have the same structure, without being limited thereto. For example, in some exemplary embodiments, light emitting diode packages having the same multiple additional functions may be disposed on the circuit board 111, or light emitting diode packages having different additional functions may be disposed on the circuit board 111, thereby providing the lighting apparatus having multiple additional functions. In addition, although an individual LED package may implement white light, in some exemplary embodiments, white light may be implemented by a combination of a plurality of LED packages.

The lighting apparatus according to exemplary embodiments may be installed not only in an indoor living space but also in an indoor space used by a plurality of people, such as a hospital or an airport. As such, a lighting system may include the lighting apparatus according to the exemplary embodiments. In this manner, this lighting system may operate to perform the additional functions described above along with a lighting function on a daily basis.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A lighting apparatus, comprising:
a controller;
an LED driver; and
an LED luminaire comprising:
a first light emitting unit configured to emit light for general lighting, the first light emitting unit including a first light emitting diode configured to emit light having a peak wavelength in a range of about 300 nm to about 470 nm and a wavelength converter; and
at least one of a second light emitting unit configured to emit light having a peak wavelength in a range of about 286 nm to about 304 nm to cause production of vitamin D upon irradiation, a third light emitting unit configured to emit light having a peak wavelength in a range of about 605 nm to about 935 nm to cause production of a cell activating substance upon irradiation, and a fourth light emitting unit configured to emit light having a peak wavelength in a range of about 400 nm to about 430 nm to sterilize pathogenic microorganisms,
wherein the controller is configured to control the LED driver to change a color temperature of the first light emitting unit in accordance with a change in a color temperature of sunlight, and to change an irradiance of light emitted from at least one of the second, third, and fourth light emitting units according to time, and
wherein the LED luminaire includes a greater number of the first light emitting unit than any of the second, third, and fourth light emitting units.

2. The lighting apparatus of claim 1, further comprising a memory configured to store data associated with a change in light intensity of at least one of the second, third, and fourth light emitting units based on a seasonal time.

3. The lighting apparatus of claim 1, wherein light emitted from the first light emitting diode and the wavelength converter implements white light.

4. The lighting apparatus of claim 3, wherein the first light emitting diode is configured to emit light having a peak wavelength in a range of about 400 nm to about 430 nm.

5. The lighting apparatus of claim 4, wherein:
the wavelength converter includes a blue phosphor; and
the white light has a first peak by the first light emitting diode and a second peak by the blue phosphor, the first and second peaks being at different wavelengths from each other.

6. The lighting apparatus of claim 5, wherein the wavelength converter further includes a green phosphor and a red phosphor.

7. The lighting apparatus of claim 3, wherein the first light emitting unit is formed in plural, each of the first light emitting units being configured to emit white light having different color temperatures from each other.

8. The lighting apparatus of claim 1, wherein the first light emitting unit is formed in plural, and white light is implemented by a combination of light emitted from each of the first light emitting units.

9. The lighting apparatus of claim 1, wherein the second light emitting unit is configured to emit ultraviolet light having a peak wavelength in a range of about 291 nm to about 301 nm.

10. The lighting apparatus of claim 9, wherein the second light emitting unit is spaced apart from the wavelength converter.

11. The lighting apparatus of claim 1, wherein the cell activating substance includes nitric oxide (NO) produced by cytochrome c oxidase activity in mitochondria.

12. The lighting apparatus of claim 11, wherein:
the wavelength converter includes a wavelength converting substance configured to convert a wavelength of light into light having a peak wavelength in a range of about 685 nm to about 705 nm, about 790 nm to about 840 nm, or about 875 nm to about 935 nm; and
the LED luminaire includes the second light emitting unit or the fourth light emitting unit.

13. The lighting apparatus of claim 11, wherein the third light emitting unit is configured to emit light having a peak wavelength in the range of about 685 nm to about 705 nm, about 790 nm to about 840 nm, or about 875 nm to about 935 nm.

14. The lighting apparatus of claim 1, wherein the peak wavelength of light emitted from the fourth light emitting unit is different from that emitted from the first light emitting diode.

15. The lighting apparatus of claim 14, wherein the peak wavelength of light emitted from the fourth light emitting unit is about 405 nm.

16. The lighting apparatus of claim 1, further comprising a circuit board on which the first light emitting unit and at least one of the second to third light emitting units are mounted.

17. The lighting apparatus of claim 1, wherein the LED luminaire comprises two or more of the second light emitting unit, the third light emitting unit, and the fourth light emitting unit.

18. A lighting system, comprising:
a lighting apparatus; and
an electronic control unit configured to input a signal into the lighting apparatus,
wherein the lighting apparatus includes:
a controller;
an LED driver; and
an LED luminaire comprising:
a first light emitting unit configured to emit light for general lighting, the first light emitting unit including a first light emitting diode configured to emit light having a peak wavelength in a range of about 300 nm to about 470 nm and a wavelength converter; and
at least one of a second light emitting unit configured to emit light having a peak wavelength in a range of about 286 nm to about 304 nm to cause production of vitamin D upon irradiation, a third light emitting unit configured to emit light having a peak wavelength in a range of about 605 nm to about 935 nm to cause production of a cell activating substance upon irradiation, and a fourth light emitting unit configured to emit light having a peak wavelength in a range of about 400 nm to about 430 nm to sterilize pathogenic microorganisms,
wherein the controller is configured to control the LED driver to change a color temperature of the first light emitting unit in accordance with a change in a color temperature of sunlight, and to change an irradiance of light emitted from at least one of the second, third, and fourth light emitting units according to time, and
wherein the LED luminaire includes a greater number of the first light emitting unit than any of the second, third, and fourth light emitting units.

19. The lighting system of claim 18, wherein the electronic control unit includes at least one of a remote controller, a mobile app, a PC, and a server.

20. The lighting system of claim 19, wherein the electronic control unit is configured to communicate with the controller wirelessly.

* * * * *